(12) United States Patent
Wang et al.

(10) Patent No.: US 12,420,104 B2
(45) Date of Patent: Sep. 23, 2025

(54) STRETCHABLE ENCAPSULATION MATERIAL WITH HIGH DYNAMIC WATER RESISTIVITY AND TISSUE-MATCHING ELASTICITY

(71) Applicant: Wisconsin Alumni Research Foundation, Madison, WI (US)

(72) Inventors: Xudong Wang, Middleton, WI (US); Yan Shao, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 644 days.

(21) Appl. No.: 17/580,890

(22) Filed: Jan. 21, 2022

(65) Prior Publication Data

US 2023/0233869 A1   Jul. 27, 2023

(51) Int. Cl.
*A61N 1/375* (2006.01)
*A61N 1/36* (2006.01)
*C08L 23/22* (2006.01)

(52) U.S. Cl.
CPC ....... *A61N 1/3758* (2013.01); *A61N 1/36014* (2013.01); *C08L 23/22* (2013.01); *C08L 2203/16* (2013.01); *C08L 2203/206* (2013.01)

(58) Field of Classification Search
CPC .................................................... A61N 1/3758
See application file for complete search history.

(56) References Cited

U.S. PATENT DOCUMENTS

| | | | |
|---|---|---|---|
| 6,169,920 B1 * | 1/2001 | Haak | A61N 1/303 604/20 |
| 11,591,501 B2 * | 2/2023 | Baetzold | H10K 59/873 |
| 12,042,661 B2 * | 7/2024 | Horn | A61N 1/3629 |
| 2018/0192952 A1 * | 7/2018 | Rogers | A61N 5/0601 |

* cited by examiner

*Primary Examiner* — George R Evanisko
(74) *Attorney, Agent, or Firm* — Boyle Fredrickson, S.C.

(57) ABSTRACT

An encapsulation for an implantable medical device is provided defined by a blend of high molecular weight polyisobutylene and low molecular weight polyisobutylene solution to provide desirable stretchability and elastic properties without sacrificing water resistance properties of the encapsulation. The encapsulation material is flexible thus allowing the medical device to possess tissue matching flexibility and retain long-term normal function free from liquid infiltration.

15 Claims, 8 Drawing Sheets

STRETCHABLE ENCAPSULATION MATERIAL WITH HIGH DYNAMIC WATER RESISTIVITY AND TISSUE-MATCHING ELASTICITY

STATEMENT REGARDING FEDERALLY SPONSORED RESEARCH OR DEVELOPMENT

This invention was made with government support under HL157077 awarded by the National Institutes of Health. The government has certain rights in the invention.

CROSS REFERENCE TO RELATED APPLICATION

--

BACKGROUND OF THE INVENTION

The present invention relates to implantable medical devices (IMDs), and more particularly, a packaging material for implantable medical devices which provides improved flexibility and water resistance.

Nanogenerators (NGs) are devices that convert mechanical or thermal energy produced from small scale physical changes into electricity. Piezoelectric generators (PGs) and triboelectric generators (TENGs) are nanogenerators that are able to convert mechanical energy into electricity. Pyroelectric generators are nanogenerators that are able to harvest thermal energy from a time dependent temperature fluctuation.

Piezoelectric generators are devices that use the piezoelectric effect of materials to harvest mechanical energy for the creation of self-powered systems. The piezoelectric effect is an electric charge that accumulates in certain solid materials in response to an applied mechanical stress, facilitating the conversion of mechanical energy to electrical energy and vice vera. This material property is a relatively common phenomenon that can be found in many organic and inorganic materials.

Triboelectric nanogenerators are devices that use the triboelectric effect of different materials to harvest mechanical energy for the creation of self-powered systems. The triboelectric effect is an electric charge that accumulates in certain materials when they are separated from a different material with which they are in contact. This material property differs for different materials and depends on their propensity to acquire a net positive charge or a net negative charge when brought into contact with each other.

Medically implantable and mountable devices have become an emerging application for nanogenerators such as piezoelectric generators and triboelectric generators that can harvests ambient mechanical energy. The piezoelectric and triboelectric materials of these nanogenerators can be used to harvest the small mechanical energy, i.e., small body motions or movement of the human body, to provide self-powered energy generation to the implantable medical devices for continuous and in vivo monitoring, diagnosis, drug delivery, or therapeutic functions. The implantable medical devices can be affixed to tissue or organ surfaces inside or outside the body.

Clinically available implantable medical devices include cardiac pacemakers, defibrillators, cochlear implants, infusion pumps, and neurostimulators. However, these implantable medical devices are typically rigid and metal-shelled bulky devices which do not allow for flexibility or movement of its internal contents. Therefore, current implantable medical device encapsulations and packages do not provide mechanical properties which allow for biomechanical motion of the flexible electronic materials therein.

SUMMARY OF THE INVENTION

Flexible implantable medical devices allow for dynamic strain of, e.g., piezoelectric and triboelectric materials, and therefore, permit biomechanical motions to be converted into electrical energy in vivo. Flexible encapsulation can be an effective way to protect flexible implantable medical devices from the physiological environment and sustain a desired average life span in vivo. Thus, complete and effective encapsulation protects the electronic components of the implantable medical device from interacting with surrounding biofluids, protects the implantable medical device from corrosion, and minimizes electricity leakage from the implantable medical devices to biological tissues. Repeated strain on the nanogenerator is required to generate continuous electricity; however, repeated strain can also result in defects in the encapsulation permitting biofluid to penetrate the encapsulation and cause electricity leakage resulting in a shorter average device life span.

Polydimethylsiloxane (PDMS) and Ecoflex® rubbers (i.e., platinum-catalyzed silicones) are commonly used packing materials for piezoelectric and triboelectric materials because of their flexibility. However, due to the high permeability of water molecules through these materials, these materials have shorter life spans when implanted inside the environment of the human body. Deposition of water impermeable thin coatings such as metal oxides, parylene, or hybrid multilayers onto the outer PDMS and Ecoflex® elastomer surfaces have been used to provide an extra barrier against water penetration, but they also increase the mechanical modulus and stiffness of the material which largely exceeds the modulus of the host tissue within the human body (e.g., 1 kPa to 1000 kPa). The addition of thin water resistant coatings also reduces the stretchability of the encapsulation compared to elastomers. Therefore, PDMS and Ecoflex® do not achieve the desired results when implanted within the human body.

The present invention provides a flexible encapsulation that can provide in vivo operation of nanogenerators and other flexible implantable medical devices and is still able to retain high water resistance under dynamic strain. The present invention provides a medically implantable or mountable device having an encapsulation or package material comprised of a blend of high molecular weight polyisobutylene (H-PIB) and low molecular weight polyisobutylene (L-PIB) materials to provide desirable stretchability and elastic properties without sacrificing water resistance properties of the encapsulation.

The flexible encapsulation or package material may match the mechanical properties of the surrounding tissue to reduce the risk of tissue injury and decrease burdens on organ functions.

The flexible encapsulation or package material may be water resistant and able to resist the penetration of water to the inside of the package.

The flexible encapsulation or package material may be able to resist breakage or defects when the implantable medical device is repeatedly bent, strained, or twisted by the movements of the body.

The flexible encapsulation or package material may be able to provide long average device life span, for example, greater than 2 weeks, 1 month, 6 months, and 12 months.

One embodiment of the present invention provides an implantable medical device comprising a flexible encapsulation adapted for retention on human tissue, the substrate having a first surface facing the human tissue and a second surface opposite the first surface wherein the encapsulation is a polyisobutylene blend of a first polyisobutylene solution having a first molecular weight and a second polyisobutylene solution having a second molecular weight; and a medical electronic device supported within the encapsulation and powered by an electrical current.

It is thus a feature of at least one embodiments of the present invention to provide a durable, water resistant encapsulation material for implantable medical devices which still retains good elasticity approximating surrounding tissue.

A molecular weight of the first polyisobutylene solution may be higher than a molecular weight of the second polyisobutylene.

It is thus a feature of at least one embodiments of the present invention to provide desirable elastic modulus modification of the encapsulation material so that the device can be matched to varying human tissue using a mixture of polyisobutylene with divergent molecular weights.

A molecular weight of the first polyisobutylene solution may be at least 100 times higher than a molecular weight of the second polyisobutylene.

It is thus a feature of at least one embodiments of the present invention to reduce the chain entanglement of long chain high molecular weight polyisobutylene and enhance the chain mobility of long chain high molecular weight polyisobutylene with the addition of short chain low molecular weight polyisobutylene.

The molecular weight of the first polyisobutylene solution may be at least 500,000. The molecular weight of the first polyisobutylene solution may be about 600,000.

It is thus a feature of at least one embodiments of the present invention to provide desirable water resistance using long chain molecules of polyisobutylene with high molecular weight. High molecular weight polyisobutylene is a rubber-like, strong elastic polymer of low tackiness, with no cold flow properties at room temperature.

The molecular weight of the second polyisobutylene solution may be less than 1000. The molecular weight of the second polyisobutylene solution may be about 920.

It is thus a feature of at least one embodiments of the present invention to provide desirable elastic modulus using polyisobutylene with low molecular weight. Low molecular weight polyisobutylene is a liquid polymer with a range of viscosities. Low molecular weight polyisobutylene promotes tack and wetting and as a result adhesion.

The weight ratio of the first polyisobutylene solution to second polyisobutylene solution may be between 2:8 to 7:3. The weight ratio of the first polyisobutylene solution to second polyisobutylene solution may be 6:4.

It is thus a feature of at least one embodiments of the present invention to adjust the elastic modulus to match or be lower than the elastic modulus of the receiving human tissue for improved biocompatibility.

The encapsulation may be flexible with an elastic modulus of less than 1000 kPa. The encapsulation may be flexible with an elastic modulus of less than 500 kPa.

It is thus a feature of at least one embodiments of the present invention to allow the elastomer to shroud a piezoelectric or triboelectric generator that relies upon the mechanical bending or flexing of the generator to harvest mechanical energy from the human body.

The medical electronic device may be an electrical generator supported within the encapsulation to convert mechanical energy harvested from movements of the skin into an electrical potential. The electrical generator may comprise a first and second dielectric material brought into contact with the movements of the skin to elicit an electric potential.

It is thus a feature of at least one embodiments of the present invention to permit a triboelectric generator to be used with the present invention as a self-generating power source.

The medical electronic device may be an electrical generator supported within the encapsulation to convert mechanical energy harvested from movements of the skin into an electrical potential. The electrical generator may include a piezoelectric material.

It is thus a feature of at least one embodiments of the present invention to permit a piezoelectric generator to be used with the present invention as a self-generating power source.

The device may include a first and second electrode supported by the encapsulation and electrically communicating with the electrical generator for receiving the electrical potential from the electrical generator wherein the first and second electrodes are flexible.

It is thus a feature of at least one embodiments of the present invention to allow the encapsulation material to protect electrical nanogenerators implanted within the human body and providing electrical insulation to the nanogenerator.

The medical electronic may be at least one of an electrical generator, sensor, actuator, and signal processor.

An alternative embodiment of the present invention provides an encapsulation material attachable to human tissue comprising a flexible encapsulation adapted for retention on human tissue, the substrate having a first surface facing the human tissue and a second surface opposite the first surface wherein the encapsulation is a polyisobutylene blend of a first polyisobutylene solution having a first molecular weight and a second polyisobutylene solution having a second molecular weight.

It is thus a feature of at least one embodiments of the present invention to permit the encapsulation material to be used for various implantable medical device applications where a flexible encasement is desirable.

An alternative embodiment of the present invention provides a method of making an encapsulation material for an implantable medical device comprising mixing a first polyisobutylene solution having a first molecular weight and a second polyisobutylene solution having a second molecular weight in hexane into a homogenous mixture; depositing the homogenous mixture into a container; drying the homogeneous mixture until the hexane is evaporated to provide a film of polyisobutylene blend; sealing a medical electronic device within films of the polyisobutylene blend.

It is thus a feature of at least one embodiments of the present invention to permit the size and thickness of the film to be scaled up at fixed ratios during the manufacture of the films.

The electrical medical device may comprise an electrical generator shrouded by an encapsulation material and converting mechanical energy harvested from movements of the skin into an electrical potential.

The method may further comprise attaching the electrical implantable medical device to human tissue in order to harvest the movements of the human tissue as a power source.

These particular objects and advantages may apply to only some embodiments falling within the claims and thus do not define the scope of the invention.

BRIEF DESCRIPTION OF THE DRAWINGS

FIGS. 5A-5F are graphical representations of the mechanical properties of polyisobutylene blend films: (FIG. 5A) Tensile strain-stress curves and (FIG. 5B) Corresponding elastic modulus (determined at <30% strain) of polyisobutylene blends with different mixing ratios and other benchmark samples including Ecoflex®, PDMS, and M-PIB (Mn=200000); (FIG. 5C) Dynamic mechanical properties; (FIG. 5D) Tensile stress—strain curves in ten cycles at 30% strain during loading-unloading cycles of polyisobutylene blends film (6:4); (FIG. 5E) Tensile strain—stress curves before and after stretching in water for 18000 times; (FIG. 5F) Tan δ spectra of polyisobutylene blend films;

FIGS. 6A-6C are graphical representations of water permeability characterizations and comparisons: (FIG. 6B) Water permeability of polyisobutylene blend film (6:4) measured at different strains; (FIG. 6C) Comparison of modulus and water permeability of polyisobutylene blend film with commonly used package materials; and FIGS. 7A-7D are graphical representations of the performance of polyisobutylene blend packaged TENG: (FIG. 7A) Voltage output of the same type of TENG packaged by four different elastomers when subjected to the same amount of tensile strain; (FIGS. 7B, 7C) Long-term in-water voltage output of TENG packaged by PIB blend (FIG. 7B) and Ecoflex (FIG. 7C). The insert of FIG. 7B is an enlarged voltage output profile within one stretching cycle; (FIG. 7D) Comparison of time-dependent peak-to-peak voltage output of TENG packaged by PIB blend and Ecoflex.

DETAILED DESCRIPTION OF THE PREFERRED EMBODIMENT

Figure 1:
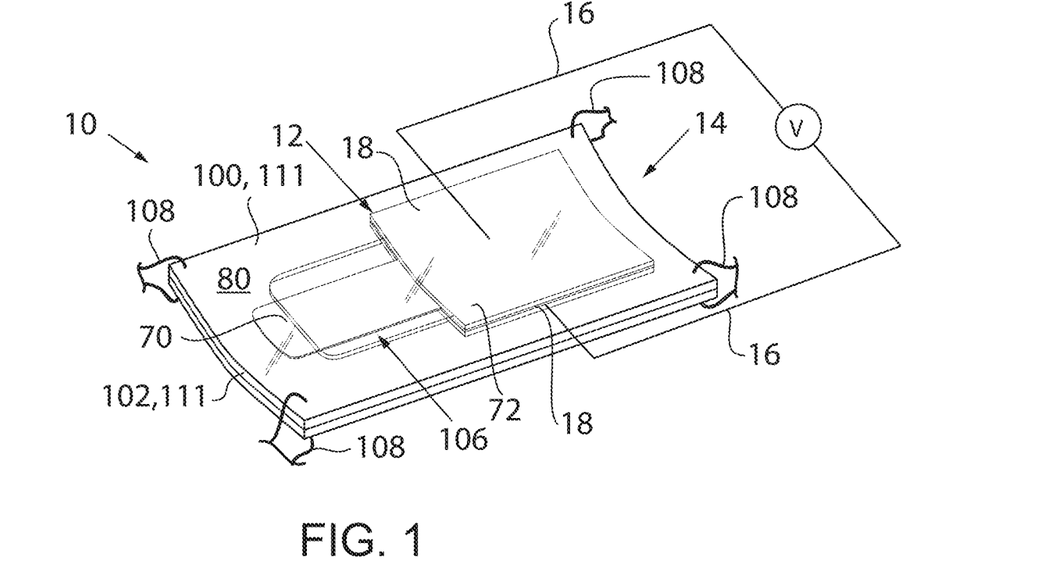
FIG. 1 is a perspective view of an implantable medical device (IMD) of one embodiment of the present invention providing a flexible outer encapsulation placed inside the body of a human patient and supporting a power generator that relies upon biomechanical motions of the body to be harvested by the power generator.

Referring to FIG. 1, an implantable medical device 10 may include a flexible medical electronic device such as an energy generator 12 supported within an outer encapsulation 14 that may be implanted inside or fixed to a human patient. The electric energy generator 12 supported by the encapsulation 14 can convert the biomechanical energy into electrical energy that is then used by, for example, an electrode pair 18 to power the implantable medical device 10. An electric potential or voltage is generated between the electrode pair 18 to power the implantable medical device 10.

The energy generator 12 held within the encapsulation package 14 may be a nanogenerator (NG) converting mechanical, thermal, or light energy produced by microscale physical changes into an electrical charge inducing an electric potential. The energy generator 12 may be a piezoelectric, triboelectric, hydroelectric, photovoltaic, or thermoelectric generator known in the art. The energy generator 12 may be "self-generating" in that it produces energy without the need for an external power source such as an alternating current (AC) or direct current (DC) power generator or a pre-charged battery as known in the art.

In one embodiment of the present invention, the energy generator 12 may harvest the movement of the patient's body or muscle motions to produce electrical energy. The movement of the body tissue and muscles may be produced by muscle stretching, breathing, blood pulsing and other voluntary and involuntary body movements of the patient. For example, slight movements of the body tissue or muscles may be captured when the patient inhales and exhales or with blood pulsing.

It is understood that the energy generator 12 is desirably lightweight with a minimized surface area to be easily implanted. An area of the energy generator 12 may have a length that is less than 2 cm and less than 1 cm and a width that is less than 2 cm and less than 1 cm. The energy generator 12 may be flexible with a thin profile commonly using soft electronic materials so that it may comply with the body's bending movements. The energy generator 12 may be less than 2 cm and less than 1 cm in thickness. The energy generator 12 may be manufactured of biocompatible material to be non-toxic to the patient when worn.

In one embodiment of the present invention, the energy generator 12 is a triboelectric nanogenerator 40 used to harvest mechanical energy from the body's movements into electricity to induce an electric potential. Generally, the triboelectric nanogenerator 40 is able to create an electric potential implantable medical device 10 by creating surface charges between two dielectric materials that exhibit opposite triboelectric polarity when touched. Once separated, the triboelectric potential between the two dielectric materials induces an electric potential on an external load, i.e., an electrode pair.

Different modes, models, and configurations of the triboelectric nanogenerator 40 may be used in connection with the present invention to produce the electric potential at the external load with certain embodiments described below. The triboelectric nanogenerator 40 is generally able to reach area power densities up to 500 W/m$^2$, volume density up to 490 kW/m$^3$, and a corresponding conversion total energy conversion efficiency of 49% to 85%.

Figure 2:
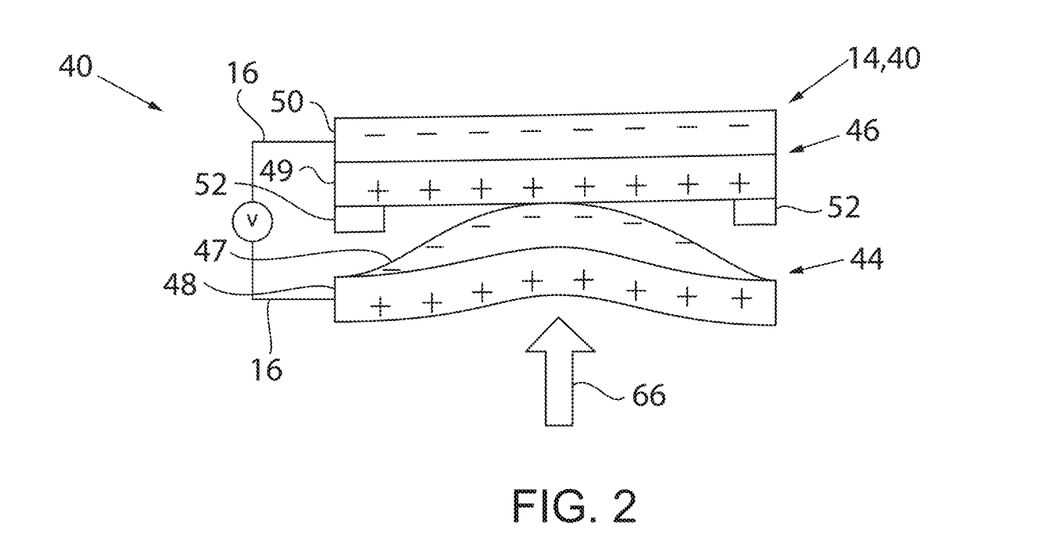
FIG. 2 is a schematic representation of one embodiment of the supported power generator of FIG. 1 showing a triboelectric device generating charge from a vertical contact and separation of oppositely charged dielectric plates.

Referring to FIG. 2, a first model of the triboelectric nanogenerator 40 is a vertical contact separation model which is based on switching between contact and separation of two oppositely charged triboelectric materials. In the contact separation model, a lower polymer sheet 44 and an upper polymer sheet 46 are assembled as a sandwiched structure where tribo-positive and tribo-negative dielectric films of the lower polymer sheet 44 and upper polymer sheet 46, respectively, form inner layers of the sandwiched structure that contact and separate with the body's movements.

The lower polymer sheet 44 includes an upper tribo-negative dielectric film 47 of triboelectrically negative dielectric material that will obtain a more negative charge when touched with another material. In one embodiment, the tribo-negative dielectric film 47 is a uniform polydimethylsiloxane (PDMS) film. Other materials that exhibit a tribo-negative charge which may be used as the upper dielectric film 47 include polytetrafluoroethylene (PTFE), polyethylene, polypropylene, vinyl (PVC), silicon, silicone rubber, ebonite and the like which are known in the art.

The tribo-negative dielectric film 47 may be patterned to form a uniform array of micro-pyramids. For example, the micro-pyramid pattern may be fabricated by curing the PDMS forming solution on silicon molds by photolithography. Instead of micro-pyramids, it is also understood that micro- or nano-cubes, lines, squares or hemispheres may also be used to enhance the contact area and the electric output. It has been found that the micro-patterns improve the mechanical flexibility and the electrical output of the triboelectric nanogenerator 40. For example, smaller micro-pyramids provide larger contact area and higher electric output.

Deposited on the back side of the tribo-negative dielectric film 47 of the lower polymer sheet 44 is a lower electrode 48 used to produce equal but opposite polarity charges formed by the electrostatic induction of the triboelectric potential generated between the positive and negative dielectric films and to connect the electric potential to the external load. In one embodiment, the lower electrode 48 is a thin layer of a metal film such as a gold film. Other conducting materials that may form the lower electrode 48 include indium tin oxide (ITO), aluminum, copper, silver, and the like which are known in the art.

The lower polymer sheet 44 contacts the upper polymer sheet 46 supporting an upper tribo-positive dielectric film 49 of triboelectrically positive dielectric material that will obtain a more positive charge when touched with another material. In one embodiment, the tribo-positive dielectric film 49 is a silk film. Other materials that exhibit a tribo-positive charge which may be used as the positive dielectric film 49 include nylon (polyamide), latex, paper, aluminum, cotton, polyester (PET) and the like which are known in the art.

Deposited on the back of the tribo-positive dielectric film 49 is an upper electrode 50. In a similar manner as the lower electrode 48, the upper electrode 50 is used to produce equal but opposite polarity charges formed by the electrostatic induction of the triboelectric potential generated between the positive and negative dielectric films and to connect the electric potential to the external load. In one embodiment, the upper electrode 50 is a metal film such as a conductive indium tin oxide (ITO) coated polyethylene terephthalate (PET) film. Other conducting materials suitable for use as the upper electrode 50 include gold, aluminum, copper, silver, and the like which are known in the art.

A spacer 52 may be inserted between the lower polymer sheet 44 and the upper polymer sheet 46 to facilitate the contact and separation of the respective sheets. The spacer 52 may be an elastic material, a foam material, an arch, or a spring, and the like formed by or placed between the lower polymer sheet 44 and upper polymer sheet 46 to provide contact and separation of the lower polymer sheet 44 and the upper polymer sheet 46.

In one embodiment, the spacer 52 may be formed of a frame layer at the outer edges of the lower polymer sheet 44 and the upper polymer sheet 46 leaving a cavity at the center between the lower polymer sheet 44 and the upper polymer sheet 46. The frame layer may be an insulating polymer sheet with double sided adhesive adhering to the lower polymer sheet 44 and the upper polymer sheet 46 at their perimeters. In another embodiment, the spacer 52 may be an arch formed by at least one of the lower polymer sheet 44 and the upper polymer sheet 46 where at least one of the lower polymer sheet 44 and the upper polymer sheet 46 is formed to naturally bend outward away from the opposite sheet so that a gap is formed between the lower polymer sheet 44 and the upper polymer sheet 46.

The contact surfaces of the tribo-negative dielectric film 47 and the tribo-positive dielectric film 49 have nanoscale roughness structures which produce friction between the two films 47, 49 thus producing opposite triboelectric charges. When an external force 66 from the body's movements bends the lower polymer sheet 44 upwards, the tribo-negative dielectric film 47 touches the tribo-positive dielectric film 49 to produce opposite charges distributed on the respective contact surfaces of the tribo-negative dielectric film 47 and tribo-positive dielectric film 49. In this respect the tribo-negative dielectric film 47 that possesses a strong electron attracting ability will develop a negative charge and the tribo-positive dielectric film 49 will develop a positive charge.

The triboelectric potential created between the dielectric films 47, 49 induces an opposite charge on the lower electrode 48 and the upper electrode 50 thus creating an electric potential between the lower electrode 48 and upper electrode 50. When the external force 66 is released, the tribo-negative dielectric film 47 and tribo-positive dielectric film 49 separate and the electric potential will neutralize. When the external force 66 is reapplied, the triboelectric potential is created again between the dielectric films 47, 49 inducing an opposite charge on the lower electrode 48 and upper electrode 50. The voltage fluctuations between the lower electrode 48 and upper electrode 50 is induced across electrical conductors 16 to the external load, e.g., an electrode pair, as further described below.

Figure 3:
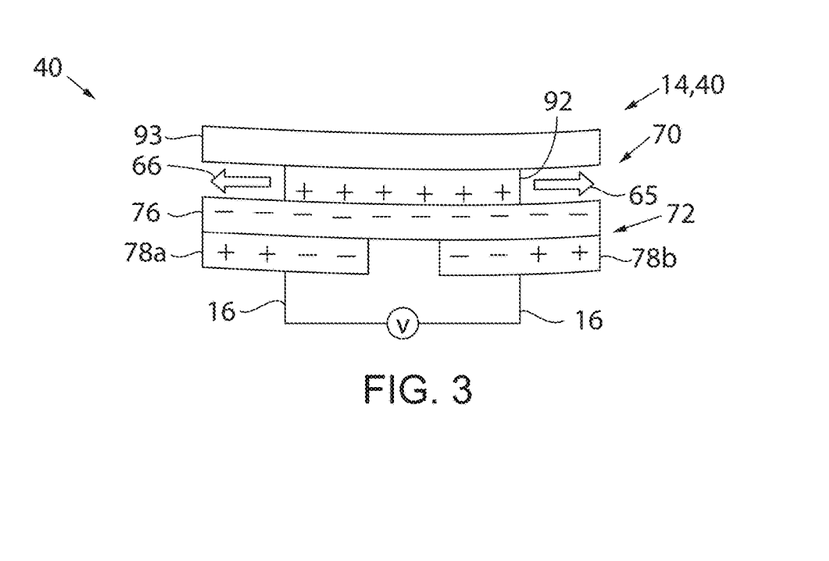
FIG. 3 is a schematic representation of an alternative embodiment of the supported power generator of FIG. 1 showing a triboelectric device generating charge from a lateral sliding of oppositely charged dielectric plates.

Referring to FIG. 3, a second model of the triboelectric nanogenerator 40 is a lateral sliding model which is based on a "freestanding" polymer sheet 70 sliding along a "stationary" polymer sheet 72 having two fixed conductors 78a, 78b deposited on the back of the stationary polymer sheet 72. In the lateral sliding model, the freestanding polymer sheet 70 and stationary polymer sheet 72 include sandwiched layers of tribo-positive and tribo-negative dielectric films which slide with respect to one another with the body's movements. The stationary polymer sheet 72 and the freestanding polymer sheet 70 may be packaged within a silicone elastomer with low friction surfaces that allow for sliding of the layers against each other with minimal resistance.

The stationary polymer sheet 72 may include a thin layer of flexible polyethylene terephthalate (PET) substrate having a tribo-negative dielectric film 76 of triboelectrically negative dielectric material contacting the freestanding polymer sheet 70 and is a material that will obtain a more negative charge when touched with another material. In one embodiment, the lower dielectric film 76 is polytetrafluoroethylene (PTFE) but may also be other tribo-negative materials such as polydimethylsiloxane (PDMS), polyethylene, polypropylene, vinyl (PVC), silicon, silicone rubber, ebonite and the like known in the art.

An opposite side of the stationary polymer sheet 72 may support a pair of conductors 78a, 78b for charge collection as the freestanding polymer sheet 70 slides along the stationary polymer sheet 72.

The stationary polymer sheet 72 slides against the freestanding polymer sheet 70, the freestanding polymer sheet 70 having a flexible polyethylene terephthalate (PET) substrate including a tribo-positive dielectric 92 of triboelectrically positive dielectric material that contacts the tribo-negative dielectric film 76 of the stationary polymer sheet 72 and is a material that will obtain a more positive charge when touched with another material. The tribo-positive dielectric 92 is deposited on a support layer 93 of polytetrafluoroethylene (PTFE).

The contact surfaces of the tribo-negative dielectric 76 of the stationary polymer sheet 72 and the tribo-positive dielectric 92 of the freestanding polymer sheet 70 have nanoscale roughness structures which produce friction between the two dielectric materials 76, 92 producing opposite charges. When the external force 66 from the body's movements slides the freestanding polymer sheet 70 along the stationary polymer sheet 72, opposite charges are distributed on the contact surfaces of the tribo-negative dielectric 76 and tribo-positive dielectric 92. In this respect the tribo-negative dielectric 76 that possesses a strong electron attracting ability will develop a negative charge and the tribo-positive dielectric 92 will develop a positive charge. Since the negative charge on the tribo-negative dielectric 76 and the positive charge on the tribo-positive dielectric 92 remain constant as the stationary polymer sheet 72 and freestanding polymer sheet 70 slide along each other, the driving force of the current is induced by the sliding of the tribo-positive dielectric 92 with respect to the pair of conductors 78a, 78b, inducing an opposite charge on the pair of conductors 78a, 78b as it moves between the pair of conductors 78a, 78b thus creating an electric potential between the pair of conductors 78a, 78b. The voltage fluctuations between the pair of conductors 78a, 78b and is induced across electrical conductors 16 to the external load as further described below.

It is understood that other modes and arrangements of the triboelectric nanogenerator 40 may be used in connection with the present invention. For example, various types of vertical contact separation mode, lateral sliding mode, and single electrode mode may be used in connection with the present invention.

The triboelectric generator 40 may be of the type described in U.S. Pat. No. 11,027,140, entitled "Self-powered, auto-responsive implanted vagal nerve stimulator for weight control" and US patent publication 2020/0316366, entitled "Electric bandage for accelerated wound recovery", both assigned to the present applicant, and hereby incorporated by reference.

Although a triboelectric nanogenerator 40 is described above, it is also understood that other types of wearable nanogenerators may also be used in connection with the present invention, for example, a piezoelectric nanogenerator may be used utilizing a nano-structured piezoelectric material or piezoelectric thin film such that when an external force is applied an electric field is produced across the piezoelectric material which can induce an electric potential across electrical conductors 16 to the external load as known in the art.

Referring again to FIG. 1, the encapsulation 14 may include a pair of rectangular encapsulation films 100, 102 casted over and under the upper and lower layers, respectively, of the triboelectric generator 40 to create at least one tissue contacting surface. The encapsulation films 100, 102 may be a similar size and joined to form a rectangular pouch or pocket enclosing the triboelectric generator 40 therein so that the triboelectric generator 40 is completely sealed and at most, only the electrical conductors 16, e.g., biocompatible leads or part of the biocompatible leads, remain exposed and extend out from the encapsulation 14.

In one embodiment, the encapsulation films 100, 102 may be formed over and under the upper and lower layers of the triboelectric generator 40, and the outer perimeter 104 of the encapsulation films 100, 102 joined together, for example, using an adhesive, to hermetically seal the encapsulation 14 around the triboelectric generator 40 within a cavity 106 of the rectangular pouch or pocket formed between the encapsulation films 100, 102 and inside the outer perimeter 104.

The encapsulation films 100, 102 may have a surface area that is greater than the surface area of the triboelectric generator 40 so that the sealed edges of the encapsulation 14 extend past the triboelectric generator 40 around a perimeter of the triboelectric generator 40 and therefore may be attached to the human tissue without disturbing or puncturing the triboelectric generator 40 or the cavity 106. For example, the sealed edges of the encapsulation films 100, 102 may extend beyond the triboelectric generator 40, particularly at opposed ends so that the encapsulation 14 may be attached, for example, by adhesive or sutures 108 as shown to the human tissue at two opposed corners or at the four corners of the rectangular encapsulation 14 without disrupting the triboelectric generator 40 or its contents and without piercing the cavity 106. Over time, the human tissue may grow over and around the implantable medical device 10 to retain the device, thus the sutures 108 may be dissolvable when they are no longer needed.

The encapsulation films 100, 102 may have a similar surface area that is at least 10% to 50% greater than an upper and lower surface area of the triboelectric generator 40. In one embodiment, the encapsulation films 100, 102 may have a surface area that is at least 10% greater and at least 20% greater, and at least 30% greater, and at least 40% greater than the upper and lower surface area of the triboelectric generator 40. The encapsulation films 100, 102 may have a length that is at least 0.5 cm and at least 1 cm and at least 2 cm, and a width that is at least 0.5 cm and at least 1 cm and at least 2 cm. The encapsulation films 100, 102 may be less than 1 mm and less than 0.5 mm in thickness. In one embodiment, the encapsulation films 100, 102 may have a length and width of 30 mm by 7 mm. The encapsulation films 100, 102 may be approximately 300 μm thick.

The cavity 106 formed between the encapsulation films 100, 102 may have a volume permitting the triboelectric generator 40 to bend or slide back and forth with the body's movements as described above with respect to FIGS. 2 and 3. The cavity 106 may have a volume that is at least 10 percent to 50 percent greater than a volume of the triboelectric generator 40 to sufficiently permit movement or flexing of the triboelectric generator inside the cavity 106. In one embodiment, the cavity 106 may have a volume that is at least 10% greater and at least 20% greater, and at least 30% greater, and at least 40% greater than the volume of the triboelectric generator 40. The cavity 106 may have a volume of at least 100 mm$^3$ and at least 150 mm$^3$ and at least 200 mm$^3$ and at least 250 mm$^3$ and at least 300 mm$^3$ and at least 350 mm$^3$ and at least 400 mm$^3$ and at least 450 mm$^3$ and at least 500 mm$^3$.

The encapsulation films 100, 102 may be manufactured from a composite material as further described below.

Further, and optionally, a layer of rubber sealant 80 may be coated on the outside of the encapsulation 14 to provide additional water resistance. The rubber sealant layer 80 may be approximately 200 μm thick. In one embodiment, the layer of rubber sealant 80 may a thin layer of Ecoflex®.

Figure 4:
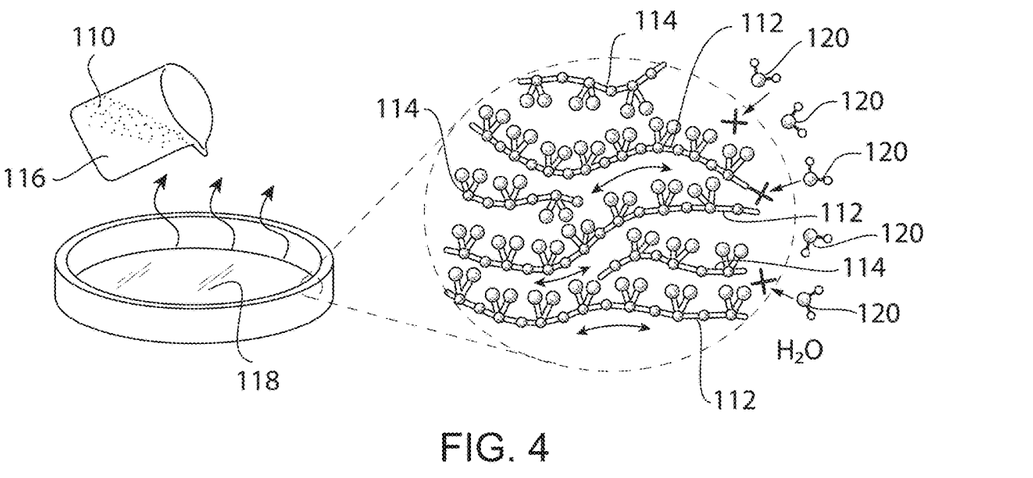
FIG. 4 is a schematic representation of the molecular structure of the encapsulation material of the flexible outer encapsulation of FIG. 1.

Referring now to FIG. 4, the material of the outer encapsulation 14 may be composed of a polyisobutylene blend 110 containing, for example, a high molecular weight polyisobutylene 112 (H-PIB) and a low molecular weight polyisobutylene 114 (L-PIB).

Polyisobutylene or polyisobutene (PM) is a class of organic polymers prepared by polymerization of isobutene. PIBs are typically colorless gummy solids and is a food and drug administration approved food ingredient commonly used as an adhesive, agricultural chemical, caulks, sealants, paper and pulp, inner tubes of tires, and chewing gum. Polyisobutylene has a low water permeability making it an ideal candidate for water resistant packing material. Polyisobutylene can also be formed in different molecular weights that span from liquid to solid with a wide range of mechanical modulus.

The polyisobutylene polymers may have the formula $Me_3C[CH_2CMe_2]_nX$ (Me=$CH_3$, X=H, F). The fully saturated nonpolar C—C backbone (which does not contain hydroxyl groups that bind with water molecules 120) of the H-PIB 112, together with the alternative small methyl groups of the L-PIB 114, offer a unique possibility to achieve both a low water permittivity and a relatively high chain mobility simultaneously.

The H-PIB 112 is chosen as the matrix and forms an entangled network to endow desired stretchable and elastic properties to the material of the outer encapsulation 14. The L-PIB 114 acts as a plasticizer to enhance the movement of molecule chains to decrease the elastic modulus of the outer encapsulation 14. The small methyl groups of L-PIB 114 are inserted between the long chains of H-PIB 112 and can achieve close contact with the long chains of H-PIB 112 without crosslinking or forming covalent bonds with each other. The addition of the L-PIB 114 minimizes tangling of the H-PIB 112 and improves the mechanical integrity of the composite material.

The outer encapsulation 14 may be manufactured by blending a solution of L-PIB 114 and a solution of H-PIB 112 to form a solution of polyisobutylene blend 110 that is further mixed with hexane solution 116. In hexane solution 116, the polyisobutylene blend 110 is stirred for about four hours to obtain a homogeneous mixture of hexane solution 116, H-PIB 112, and L-PIB 114. The hexane solution 116, H-PIB 112 (Mn: 600,000) and L-PIB 114 (Mn: 920) may be supplied by Millipore Sigma/Signa-Aldrich of Darmstadt, Germany.

A solid film of polyisobutylene blend 111 may be prepared by casting the homogenous mixture of polyisobutylene blend 110 with hexane solution 116 onto a flat surface. The homogenous mixture of polyisobutylene blend 110 with hexane solution 116 may be casted onto a petri dish surface 118 to a pre-defined thickness. The thickness of the solid film of polyisobutylene blend 111 may be controlled by applying more blended solution of L-PIB 114 solution with a H-PIB 112 solution into the petri dish surface 118 or container surface. The film 111 is dried in atmosphere at room temperature until all solvent is completely evaporated and transparent polyisobutylene blend solid film 111 is achieved. The size of the solid film of polyisobutylene blend 111 may be made to any desirable surface area size, allowing the encapsulation 14 to be scaled up for large scale production with the film of polyisobutylene blend 110 retaining the same fixed ratio of L-HIB and H-PIB 112.

The polyisobutylene blend 110 combines two different and divergent molecular weights of polyisobutylene in order to achieve the desired modulus modification. The desired elastic modulus may match or is lower than the human tissue to which the implantable medical device 10 is attached.

In one embodiment of the present invention, the polyisobutylene blend 110 may include L-PIB 114 with a molecular weight that is between 350-2400 and less than 3000 and less than 2000 and less than 1000. The polyisobutylene blend 110 may further include H-PIB 112 with a molecular weight that is between 75,000-1,000,000 and greater than 50,000 and greater than 100,000 and greater than 150,000. The polyisobutylene blend 110 may include H-PIB 112 and L-PIB 114 where the molecular weight of the H-PIB 112 may be at least 30 times greater and at least 50 times greater and at least 100 times greater and at least 200 times greater and at least 300 times greater and at least 400 times greater and at least 500 times greater and at least 600 times greater and at least 700 times greater and at least 700 times greater and at least 800 times greater and at least 900 times greater and at least 1000 times greater than the molecular weight of the L-PIB. In one embodiment of the present invention, the L-PIB 114 may have a molecular weight of about 920 and the H-PIB 112 may have a molecular weight of about 600,000 and the H-PIB is at least 650 times greater than the molecular weight of the L-PIB.

Polyisobutylene is commercially available in the following molecular weight categories: L-PIB (MW: 200-10000); M-PIB (MW: 20000-45000); H-PIB (MW: 75000-600000); and super high PM (MW: >760000). In one embodiment, the present invention blends two different molecular weight categories of polyisobutylene to form the polyisobutylene blend 110. For example, the polyisobutylene blend 110 may blend L-PIB (MW: 200-10000) with H-PIB (MW: 75000-600000) but could alternatively blend any combination of divergent PM molecular weight categories such as lower molecular weight L-PIB (MW: 200-10000) or medium molecular weight M-PIB (MW: 20000-45000) with higher molecular weight H-PIB (MW: 75000-600000) or super high PM (MW: >760000). The use of L-PIB (MW: 200-10000) may be desirable within the mixture since L-PIB (MW: 200-10000) is present in liquid form and thus is easier to mix with the other high molecular weight category of polyisobutylene. Although the abbreviations "H-PIB" and "L-PIB" are used throughout the application to refer to a high molecular weight polyisobutylene 112 and a low molecular weight polyisobutylene 114, respectively, it is understood that H-PIB 112 and L-PIB 114 may refer to any combination of a high molecular weight polyisobutylene and a low molecular weight polyisobutylene and not necessarily the commercially available molecular weight categories of "H-PIB (MW: 75000-600000)" and "L-PIB (MW: 200-10000)" described in this paragraph.

The polyisobutylene blend 110 may use different L-PIB 114 to H-PIB 112 weight ratios, ranging from 2:8 to 7:3 to achieve desired mechanical properties and elastic modulus. Polyisobutylene blend 110 may be prepared with different weight ratios of, for example, 2:8, 3:7, 4:6, 5:5, 6:4 and 7:3 (L-PIB 114 to H-PIB 112) by solution blending of different amounts of H-PIB 112 and L-PIB 114. The different weight ratios will result in varying elastic moduli of the solid film. In one embodiment, the polyisobutylene blend 110 has an elastic modulus of 4:6 (L-PIB 114 to H-PIB 112).

The elastic modulus of the polyisobutylene blend solid film 111 may be between 1 kPa and 1000 kPa to approximately match or be lower than the elastic modulus of the surrounding human tissue or biological material on which the implantable medical device 10 is attached or implanted. For example, the polyisobutylene blend 110 used with the implantable medical device 10 have an elastic modulus of 5 kPa to 10 kPa if attached to human skin, and may have an elastic modulus of 10 kPa to 15 kPa if attached to the human heart or other muscles, and may have an elastic modulus of 30 to 50 kPa if attached to a human tendon. In one embodiment, the polyisobutylene blend solid film 111 has an elastic modulus than is less than 1000 kPa and less than 500 kPa and less than 100 kPa and less than 10 kPa in order to provide elastic moduli in ranges resembling human tissues or is lower than common ranges of human tissue.

EXAMPLES

Example 1: Polyisobutylene Blend with Weight Ratio of 6:4 (L-PIB to H-PIB)

In one embodiment of the present invention, the modulus of polyisobutylene blend solid film 111 at the L-PIB 114 to H-PIB 112 weight ratio of 6:4 demonstrated an elastic modulus of 62 kPa, matching or lower than those of most body tissues. No phase separation features were seen from the film surfaces and cross-section, as revealed by uniform contrast under scanning electron microscopy (SEM), suggesting that L-PIB 114 molecules distributed well within the network of entangled long H-PIB 112 molecular chains. As a result, the polyisobutylene blend solid films 111 exhibited a uniformly high transparency.

Fourier transform infrared spectroscopy (FTIR) of the polyisobutylene blend solid films 111 showed the same characteristic absorption peaks of the polyisobutylene chains. No new peaks were observed from the polyisobutylene blend solid film 111, indicating there were no new chemical interactions between the molecular chains of H-PIB 112 and L-PIB 114 after blending. The FTIR spectra was measured by a Nicolet iS50R FTIR spectrophotometer on pristine H-PIB 112 film and polyisobutylene blend solid film 111 with weight ratio 6:4.

To confirm that the desired hydrophobicity of pristine H-PIB 112 was not changed after blending with L-PIB 114, water contact angles of the polyisobutylene blend solid films 111 were measured and compared with pristine H-PIB 112 films. The contact angles of water droplets on the material surfaces were measured using a contact angle system at room temperature. The 5 μL of deionized water droplets were applied to the film surface by the automatic dispenser of the contact angle system. The contact angles were determined from the side-view images of dispensed water droplets. The polyisobutylene blend solid films 111 exhibited a very close water contact angle at approximately 113°, confirming that short chain L-PIB 114 had negligible influences to the hydrophobic property of long chain H-PIB 112, which is preferred for achieving good protection in physiological environment.

Example 2: Measuring Static Tensile Properties at Different Weight Ratios

In one embodiment of the present invention, the static tensile properties, dynamic modulus, and temperature sweep measurements were characterized by an RSA III dynamic mechanical analyzer using a rectangular geometry. All the films for mechanical property testing were made in a rectangular shape with a size of 30 mm by 7 mm and a thickness of 300 μm.

The static tensile properties were characterized at room temperature at a strain rate of 50 mm/min. The stress-strain curves were measured using a transient force gap method.

The films of polyisobutylene blend 110 with different L-PIB 114 to H-PIB 112 weight ratios (i.e., 3:7, 5:5, 7:3, 2:8, 4:6, 6:4) all exhibited smooth and homogeneous surfaces with a high transparency. All the polyisobutylene blends exhibited excellent stretchability and survived under large stains of at least 75%, suggesting the integration of L-PIB 114 did not jeopardize the integrity of long chain polyisobutylene networks. All the polyisobutylene blends 110 showed a typical elastomer behavior.

Figure 5A:
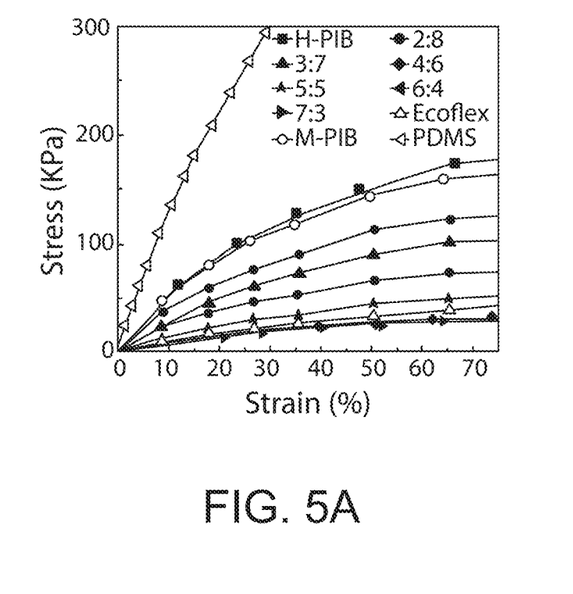

Referring to FIG. 5A, the stress-strain curves were measured from all polyisobutylene blend solid films 111 with an identical rectangular shape (30 mm by 7 mm by 0.3 mm) at a strain rate of 50 mm/min. The same measurement was also conducted on the same sized films of PDMS, Ecoflex® and medium molecular weight polyisobutylene (M-PIB, molecular weight ~200,000, which was close to the median of L-PIB 114 and H-PIB 112). The strength of the film of polyisobutylene blend 110 decreased as the content of L-PIB 114 increased in the polyisobutylene blend 110. The stress-strain relationships of all weight ratios were mostly linear within the strain range of 0-30% and then slightly tapered off as strain further increased.

It was found that for one single type of polyisobutylene with a medium molecular weight (M-PIB) that was similar to the average of the L-PIB 114 and H-PIB 112 blend at the weight ratio of 6:4, the interaction among molecules was still strong and the elastic modulus (350 kPa) was only slightly smaller than that of H-PIB 112.

Figure 5B:
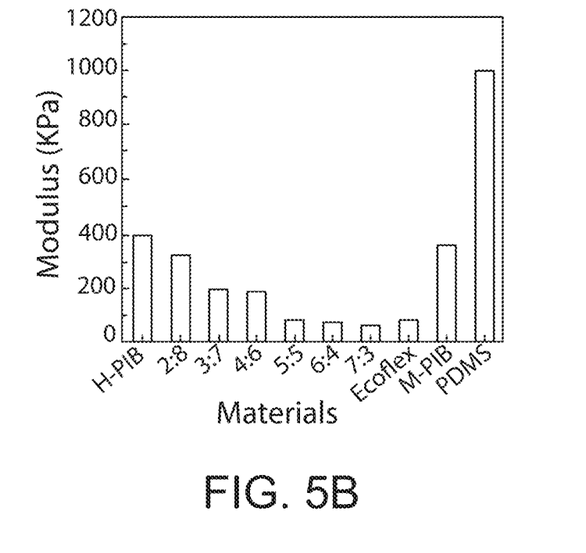

Referring to FIG. 5B, the elastic modulus of all the samples were determined from the slope within the linear range. The elastic modulus of pristine H-PIB 112 was about 400 kPa. As L-PIB 114 was added, the modulus of polyisobutylene blend solid films 111 decreased monotonically. When the weight ratio was 6:4, the modulus reached as low as 62 kPa. Further increases in the L-PIB 114 content to 7:3 in the blend exhibited minimal impacts to the elastic modulus.

The introduction of short chain L-PIB 114 reduced chain entanglement of H-PIB 112 and enhanced the chain mobility of H-PIB 112, and thereby reduced the materials' elastic modulus. The 6:4 ratio appears to be the maximum point where the freedom of long-chain H-PIB 112 could be reached by L-PIB 114 facilitation. Therefore, it is desirable to blend the two molecular weight types of polyisobutylene with divergent molecular weights in order to achieve desired modulus modification.

As comparative packaging elastomers, Ecoflex® and PDMS have a modulus of 70 KPa and 1 MPa, respectively within the measurement range, which could be reached and are surpassed by the polyisobutylene blends with a 6:4 weight ratio and above.

Example 3: Measuring Dynamic Mechanical Properties of Polyisobutylene Blend

The dynamic moduli were measured at the frequency of 1 Hz at room temperature within a strain range from 1% to 10%. For temperature sweep measurement, the films were fixed on a tension clamp and strained to 0.1% at a frequency of 1 Hz, where the temperature was swept from −90° C. to 0° C. at a heating rate of 2.5° C./min.

Figure 5C:
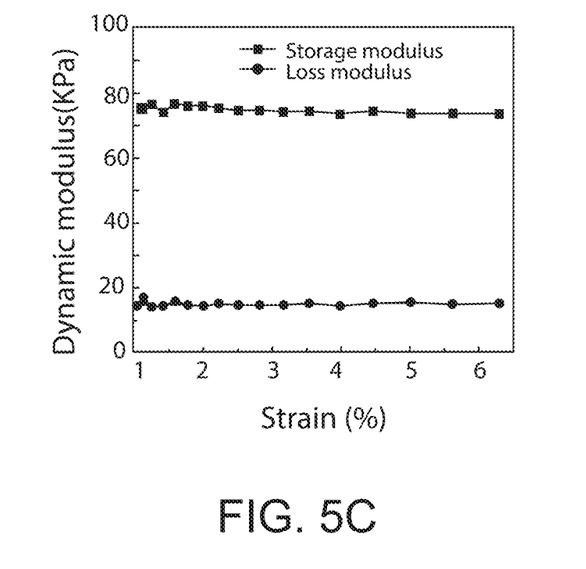

Referring to FIG. 5C, the dynamic modulus of the polyisobutylene blend solid film 111 (6:4) was tested under varying strains ranging from 1% to 7% at 1 Hz. The storage modulus (~75 kPa) and loss modulus (~15 kPa) remained stable across the entire testing strain range, indicating the polyisobutylene blend solid film 111 was able to function normally under a consecutive straining condition. The substantially larger storage modulus compared to the loss modulus demonstrated that the polyisobutylene blend solid film 111 had a characteristic elastic property.

Figure 5D:
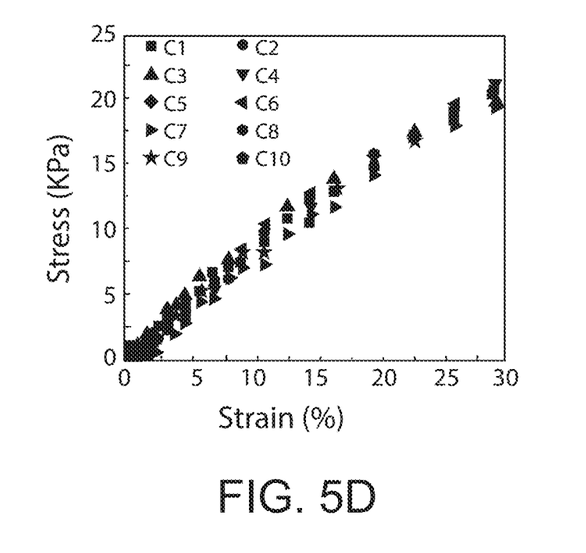

Referring to FIG. 5D, the repeating cycling test presented a good reproducibility of the stress-strain curves of polyisobutylene blend solid film 111 (6:4), evidencing the solid film's stable mechanical property during multiple loading-unloading cycles.

Figure 5E:
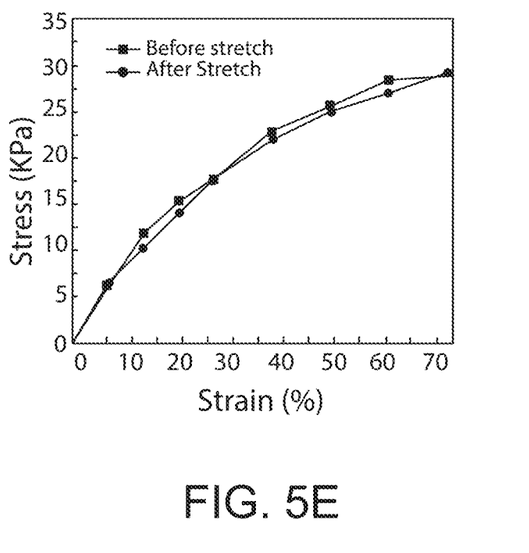

Referring to FIG. 5E, to further evaluate the mechanical stability of the polyisobutylene blend solid film 111 (6:4) in an aqueous environment, the polyisobutylene blend solid film 111 was stretched repeatedly in water to a strain of 30% for 18,000 cycles at a frequency of 1 Hz. The stress-strain curves were measured before and after the endurance test. Identical mechanical behavior was obtained, confirming the polyisobutylene blend solid film 111 could retain a high mechanical stability after long-term stretching operation in water.

Figure 5F:
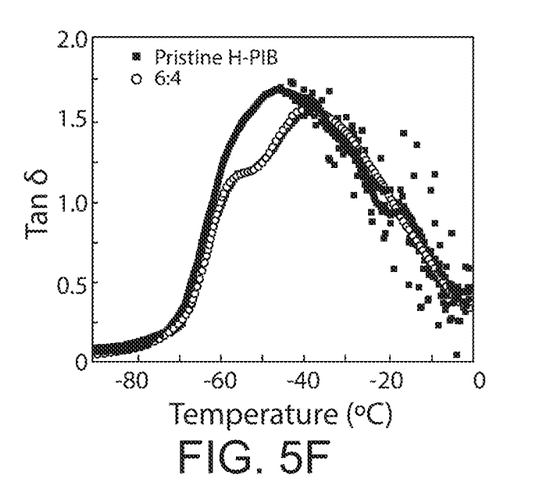

Referring to FIG. 5F, temperature sweeps of the dynamic mechanical properties were conducted to determine the glass transition temperature ($T_g$) within the temperature range from −90 to 0° C. at 1 Hz. A sharp peak of tan δ was observed at −38° C. and −45° C. for pristine H-PIB 112 and pristine polyisobutylene blend solid film 111 (6:4), respectively, which correspond to their $T_g$. Shift of $T_g$ to lower temperature indicates that blending L-PIB 114 into H-PIB 112 improves the segmental mobility. This is also supported by the reduced storage modulus (E') and loss modulus (E") from the polyisobutylene blend 110 compared to pristine H-PIB 112. In addition, only one $T_g$ peak was identified from the polyisobutylene blend solid film 111, which also indicated the good homogeneity of polyisobutylene blend solid films 111.

Example 4: Testing Water Transmission Rate

The gravimetric method was used to determine the water transmission rate of all the polyisobutylene blend solid films 111 at room temperature. The film samples were placed over the mouth of vials prefilled with anhydrous copper sulfate. The film edges were sealed by a paraffin film to the mouth of vials, and further tightened by a hollow lid. All the vials had a diameter of 1 cm. After applying the film, the vial was placed in a beaker filled with deionized water for three weeks. The vial was then removed from water and its weight increment was measured immediately.

The water transmission rate was calculated using the equation: WTR=Δm/A/t, where Δm was the weight increment of the vial (g), A was the exposed film surface area ($m^2$), and t was the total time being immersed in water (day). Three tests were conducted for each type of film and the mean value was reported.

Figure 6A:
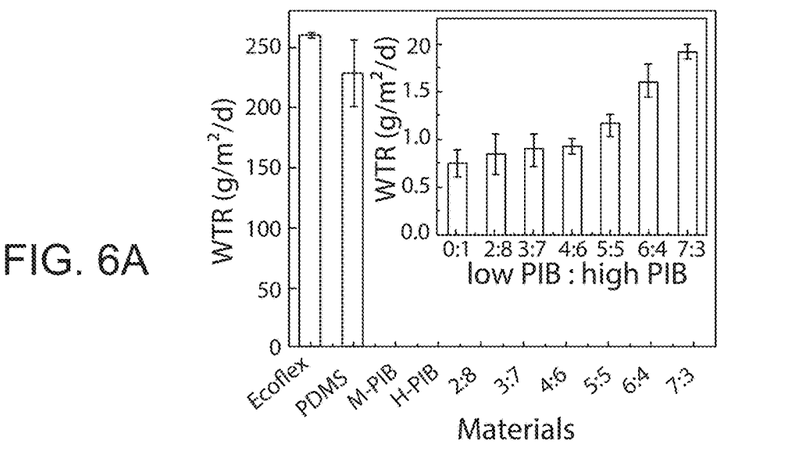
(FIG. 6A) Water permeability measured at 0% strain from polyisobutylene blend films with different ratios in comparison to other commercial packaging elastomers, the insert was an enlarged scale from FIG. 6A to show the water permeability of all polyisobutylene blend films.

Referring to FIG. 6A, the essential function of the encapsulation 14 for implantable nanogenerators is to prevent body fluid infiltration. The water permeability of all polyisobutylene blend solid films 111 and a few commercial packaging elastomers was measured by the gravimetric method using glass vials filled with desiccant over a three-week period. All the film samples had the same thickness of 300 μm. Each sample was measured three times to obtain the mean values and standard deviations.

The water permeability of Ecoflex® and PDMS was found to be 260 $gm^{-2}$ $day^{-1}$ and 230 $gm^{-2}$ $day^{-1}$, respectively, whereas all the polyisobutylene blends films exhibited water permeability at the level of about 1 $gm^{-2}$ $day^{-1}$.

The more than two orders of magnitude lower water permeability of polyisobutylene blend 110 can be attributed to the combined effect of the nonpolar C-C chain and dense small pendant methyl groups. Compared to the silicon-based elastomers, the repeating C-$CH_3$ units offer weaker intermolecular interaction with water molecules and reduce their adsorption. In addition, the small and dense pendant methyl groups on main C-C chain minimized the internal free-volumes, further restricting the diffusion of water molecules.

The water permeability increased monotonically following the L-PIB 114 ratio. The pristine H-PIB 112 showed the lowest water permeability of 0.75±0.14 $gm^{-2}$ $day^{-1}$, which increased to 1.6±0.18 $gm^{-2}$ $day^{-1}$ for polyisobutylene blend solid film 111 at 6:4. This result is because the short chain L-PIB 114 facilitates the overall polymer chain motions, and thus provides more accessible internal free-volumes allowing water molecules to diffuse through. Despite this small increment, the polyisobutylene blend film still had substantially enhanced the water resistivity behavior compared to Ecoflex® and PDMS.

Figure 6B:
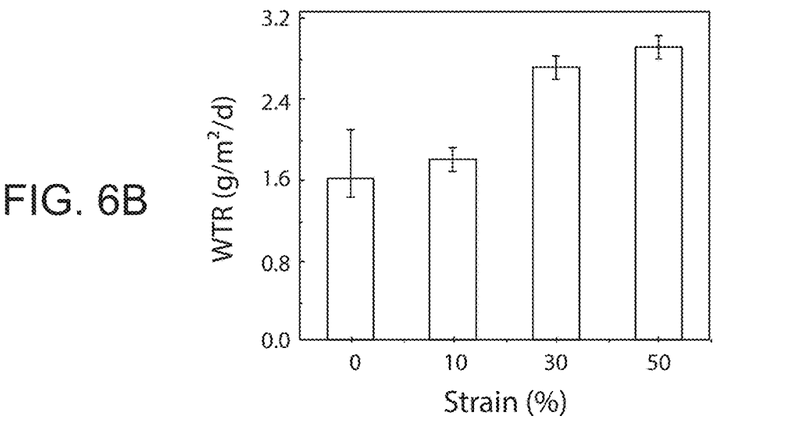

Considering the devices need to work under dynamic straining conditions, the water permeability of the polyisobutylene blend film (6:4) was further tested under a series of static strains.

Referring to FIG. 6B, the water permeability slightly increased from 1.6±0.18 $gm^{-2}$ $day^{-1}$ to 2.9±0.1 $gm^{-2}$ $day^{-1}$ as the strain increased from 0 to 50%. This could be attributed to the small thickness reduction. Nevertheless, the generally low $H_2O$ adsorption and diffusion ensured the very low water permeability compared to other materials.

Figure 6C:
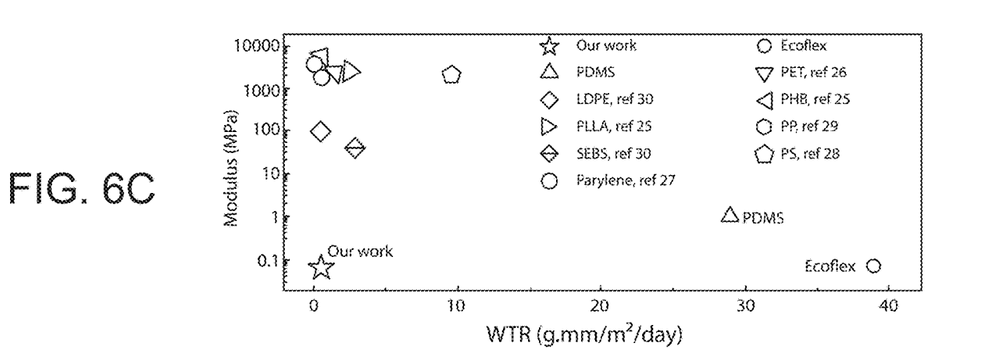

Referring to FIG. 6C, the unique combination of high flexibility and low water permeability brought a substantial advantage for the polyisobutylene blend films to be used as a stretchable packaging material for flexible nanogenerators. To demonstrate this advantage, a scatter plot was constructed to compare the modulus and water permeability of the polyisobutylene blend solid film 111 to other state-of-the-art commercial or literature-reported packaging materials.

The polyisobutylene blend solid film 111 resides uniquely at the lower left corner. Ecoflex®, a commercial elastomer with a similar modulus, had substantially higher water permeability. Typical water insulating packaging materials, such as PHB, PP and LDPE, had a similar level of water permeability, but their moduli are all in the GPa range, ~3-5 orders of magnitude higher than our polyisobutylene blends. This comparison demonstrated that only the polyisobutylene blend 110 can satisfy both high water resistance and tissue-like mechanical property requirements simultaneously for the development of implantable nanogenerators.

The film of polyisobutylene blend 110 demonstrates excellent encapsulation performance in an aqueous environment under dynamic mechanical strains, allowing the packaged nanogenerator to operate continuously for at least two weeks in the aqueous environment, substantially surpassing the protection offered by Ecoflex®.

Example 5: Encapsulation of Sliding Mode Teng within Polyisobutylene Blend

Referring again to FIGS. 1 and 3, to demonstrate the unique advantage of the polyisobutylene blend 110 encapsulation material, a simple sliding mode triboelectric nanogenerator 40 was fabricated and packaged within the polyisobutylene blend solid films 111.

PTFE film and Cu film was used as the triboelectric layers to fabricate a sliding mode triboelectric nanogenerator 40. PET (0.7×3.5 cm2, 300 μm thickness, CS Hyde Company, USA) was used as the substrate, and Cu tape (100 μm) was attached on both sides of the PET film to act as the mobile layer. A thin PTFE film (2.5×1 cm2, 50 μm, CS Hyde Company, USA) with attached Cu electrode was used as the static part. The sliding mode triboelectric nanogenerator 40 was assembled by attaching two PTFE/Cu films along the edges with the PTFE surface facing each other. The Cu/PET/Cu mobile layer was inserted between the two PTFE/Cu films.

The polyisobutylene blend solid film 111 with weight ratio of 6:4 was used to package the sliding mode triboelectric nanogenerator 40. A thin film of Ecoflex® (Reynolds Advanced Materials, Inc., USA, 30-40 μm in thickness) was also coated on the outside of the encapsulation 14. The total package of polyisobutylene blend solid film 111 had a thickness of 300 μm. The outer edge was sealed by hot compression at a temperature of 140° C.

For comparison, the same triboelectric nanogenerator 40 were also packaged by 300 μm Ecoflex®. Ecoflex® film was made by spin-coating a solution consisting of parts A and B (1:1 by weight) at a speed of 500 rpm for 30 seconds. As a result, Ecoflex® film with the thickness of ~300 μm was achieved. The polyisobutylene blend solid film 111 was wrapped around the triboelectric nanogenerator 40, and uncured Ecoflex® solution was applied to the joint edge for adhesion. The outer edges of the polyisobutylene blend solid films 111 were then sealed by hot compression at a temperature of 90° C.

The sliding mode triboelectric nanogenerator had two parts: a center mobile layer 70 made from Cu film and top/bottom stationary layer(s) 72 composed of a PTFE film 76 covered by a Cu electrode 78a, 78b. The entire triboelectric nanogenerator 40 was completely packaged by a 300 μm polyisobutylene blend solid film 111 with each side kept at ~3 mm from the triboelectric nanogenerator 40 device. The polyisobutylene blend solid film 111 was tightly attached to the Cu electrode surface 78a, 78b and the front portion of the center mobile layer 70 surface by hot press. A space of 2 cm between the fixed areas on the Cu electrodes 78a, 78b and the mobile layer 70 was left unattached, forming a stretchable cavity 106 allowing free lateral motion of the center mobile layer 70. The packaged triboelectric nanogenerator 40 was operated by pulling the center mobile layer 70 back and forth, and the output voltage was measured from the Cu electrodes 78a, 78b.

To compare the performance of polyisobutylene blends 110, the same triboelectric nanogenerator 40 with the same voltage output were packaged by three common packaging elastomers, i.e., Ecoflex®, PDMS and Polyethylene (PE). All the package layers had the same size and thickness.

Figure 7A:
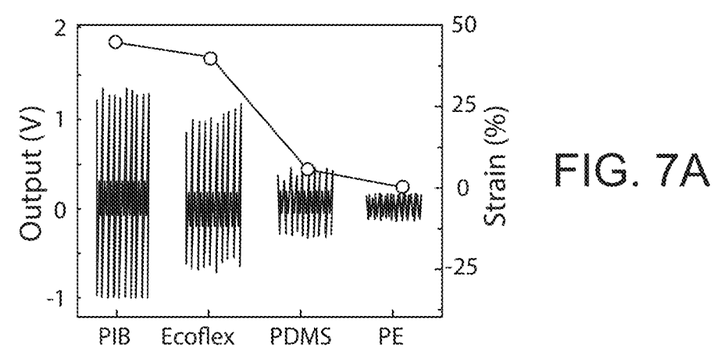

All the triboelectric nanogenerators 40 were first tested under the same pulling force of ~0.49 N. Due to the different elastic modulus of the packaging materials, the same pulling force induced different level of displacement (strain) at the stretchable cavity, where the polyisobutylene blend-packaged triboelectric nanogenerator 40 demonstrated the highest strain of 45%. Accordingly, it also generated the highest voltage output with a peak-to-peak value ($V_{pp}$) of ~2.2 V (FIG. 7A). Ecoflex®, with a slightly lower modulus, exhibited a close strain of 40% and a slightly lower $V_{pp}$ of ~1.6 V. The strain and $V_{pp}$ drastically dropped to 5.5% and ~0.8 V, respectively for the PDMS-packaged triboelectric nanogenerator 40 as its modulus was 16 times higher than that of the polyisobutylene blend film. The much more rigid PE (1.5 GPa) package yielded a negligibly low strain and voltage outputs. This comparison revealed the significance of a low elastic modulus for the packaging material for the operation of flexible implantable nanogenerators, as the available driving force from body tissue movements is rather limited.

Figure 7B:
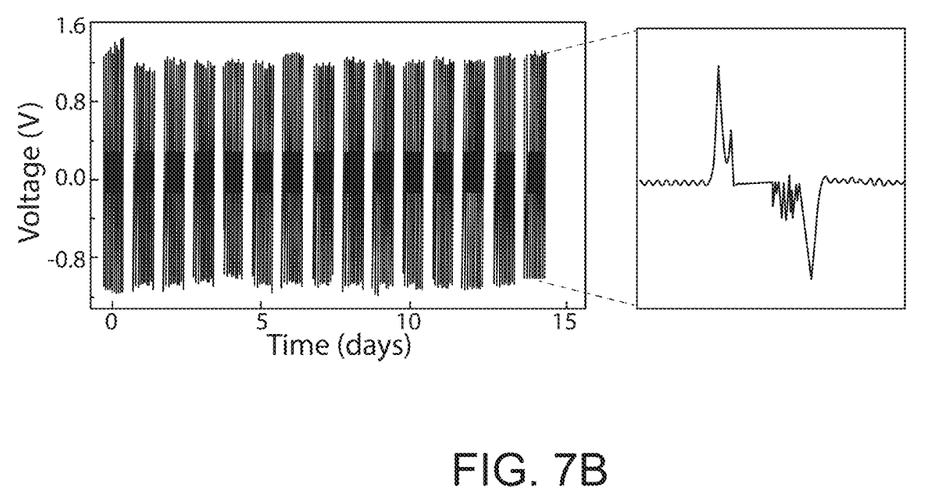

Considering the practical application conditions of implantable nanogenerators, the long-term protection of polyisobutylene blend 110 was evaluated under continuous dynamic deformation.

FIG. 7B shows the recorded voltage output profiles of the polyisobutylene blend-packaged triboelectric nanogenerator 40 over 15 days. The device was repeatedly stretched to a 30% strain and released at 1 Hz in deionized water. The day 0 signal was voltage outputs measured before soaking in water. The device was able to retain its original output for 2 weeks, demonstrating an excellent water barrier property and electric resistance of polyisobutylene blends. The output dropped to zero on day 15 however this was because of a wearing out at the contact point with the anchoring base which was needed for in-water straining test. A much longer protection period can be expected in practical applications when no wearing at anchoring contact points are involved.

Figure 7C:
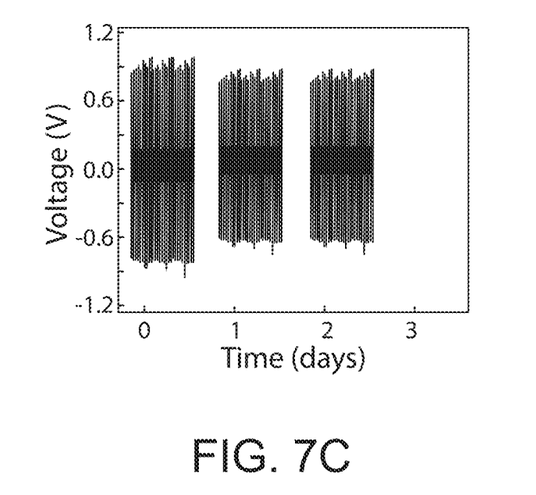

As Ecoflex® offers the same level of flexibility as polyisobutylene blends, comparison was conducted on Ecoflex-packaged triboelectric nanogenerators 40 under the same testing conditions. As shown in FIG. 7C, the voltage output dropped drastically after immersing in water for just two days and the device completely failed on day 3.

Figure 7D:
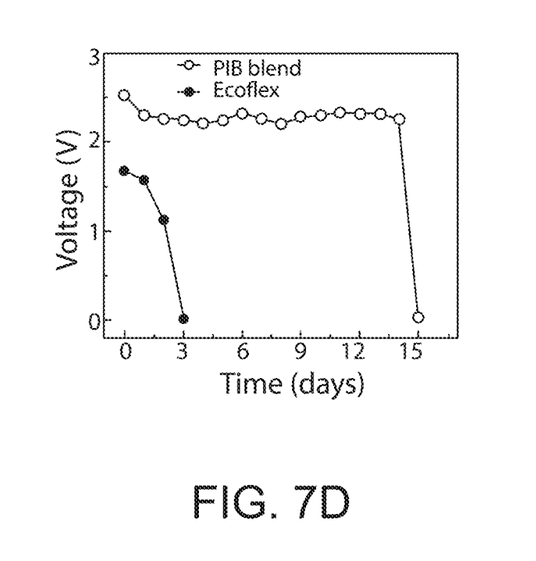

The time-dependent $V_{pp}$ of both polyisobutylene blend and Ecoflex-packaged triboelectric nanogenerators 40 were plotted in FIG. 7D. It was revealed that the polyisobutylene blend solid films 111 were able to offer substantially longer and stable protection than Ecoflex® under a dynamic straining action in an aqueous environment.

It is understood that although particular embodiments and combinations of the implantable medical device 10, electric energy generator 12, and electrode conductors 16 are shown and described above, it is understood that any combination of the implantable medical device 10, electric energy generator 12, and electrode conductors 16 may be used with respect to application of the present invention.

It is understood that the power electronics of the electric energy generator 12 may be substituted with other medical device implantable electronics associated with, e.g., sensors, actuators, and signal processing of commonly known implantable medical device. These medical device implantable electronics are powered by an electrical current and therefore are desirably electrically insulated by the outer encapsulation 14 and waterproofed by the outer encapsulation 14 to prevent ingress of fluid to the electronics. For example, the medical implantable electronics used with the present invention may be a flexible radio frequency (RF) tag that receives microwave information, an electrode circuit that receives electromagnetic waves for remote charging, a passive electro resistive sensor, or stimulation electrode arrays, or other flexible electronic medical devices known the art.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. An implantable medical device comprising:
    a device body;
    a flexible encapsulation adapted for retention on human tissue, the encapsulation providing an encapsulation film adapted to surround the device body and having a first surface configured to face the human tissue and a second surface opposite the first surface;
    wherein the encapsulation film:
        is a polyisobutylene blend comprising:
            a first polyisobutylene component comprising H-PIB (high molecular weight polyisobutylene) having a first molecular weight from 75,000 to 600,000 and
            a second polyisobutylene component comprising L-PIB (low molecular weight polyisobutylene) having a second molecular weight that is less than 3,000; and
        wherein the first molecular weight of the first polyisobutylene component H-PIB is at least 200 times greater than the second molecular weight of the second polyisobutylene component L-PIB.

2. The device of claim 1 wherein the molecular weight of the first polyisobutylene component is at least 500,000.

3. The device of claim 1 wherein the molecular weight of the first polyisobutylene component is about 600,000.

4. The device of claim 1 wherein the molecular weight of the second polyisobutylene component is less than 1000.

5. The device of claim 1 wherein the molecular weight of the second polyisobutylene component is about 920.

6. The device of claim 1 wherein the weight ratio of the first polyisobutylene component to second polyisobutylene component is between 2:8 to 7:3.

7. The device of claim 1 wherein the weight ratio of the first polyisobutylene component to second polyisobutylene component is about 6:4.

8. The device of claim 1 wherein the encapsulation is flexible and has an elastic modulus of less than 1000 kPa.

9. The device of claim 1 wherein the encapsulation is flexible and has an elastic modulus of less than 500 kPa.

10. The device of claim 1 wherein the device body comprises a first dielectric material and a second dielectric material configured to move with respect to each other with the movements of the skin to elicit an electric potential.

11. The device of claim 1 wherein the device body comprises a piezoelectric material.

12. The device of claim 1 wherein the device body houses at least one of an electrical power generator, sensor, actuator, and a signal processor.

13. The device of claim 1, wherein:
    the first molecular weight of the H-PIB is about 600,000; and
    the second molecular weight of the L-PIB is from 350 to 2,400.

14. The device of claim 13 wherein:
    the encapsulation film has an elastic modulus from 1 kPa to 1,000 kPa;
    the weight ratio of the first polyisobutylene component to second polyisobutylene component is between 2:8 to 7:3; and
    the first molecular weight of the first polyisobutylene component is at least 600 times greater than the second molecular weight of the second polyisobutylene component.

15. An encapsulation attachable to human tissue comprising:
    a flexible encapsulation body adapted for retention on human tissue, the encapsulation body having a first surface attachable to the human tissue and a second surface opposite the first surface and providing a cavity between the first surface and second surface;
    wherein the encapsulation body comprises a material that is a polyisobutylene blend of:
        a first polyisobutylene component having a first molecular weight from 75,000 to 600,000; and
        a second polyisobutylene component having a second molecular weight that is less than 1,000; and
    wherein the first molecular weight of the first polyisobutylene component is at least 200 times greater than the second molecular weight of the second polyisobutylene component.

* * * * *